United States Patent [19]

Kaufhold et al.

[11] Patent Number: 5,008,429
[45] Date of Patent: Apr. 16, 1991

[54] PROCESS FOR INDUSTRIAL APPLICATION OF KNOEVENAGEL SYNTHESIS

[75] Inventors: Manfred Kaufhold; Josef Metz, both of Marl, Fed. Rep. of Germany

[73] Assignee: Huels Aktiengesellschaft, Marl, Fed. Rep. of Germany

[21] Appl. No.: 446,601

[22] Filed: Dec. 6, 1989

[30] Foreign Application Priority Data

Mar. 18, 1989 [DE] Fed. Rep. of Germany ....... 3908998

[51] Int. Cl.$^5$ ............................................ C07C 253/30
[52] U.S. Cl. .................................. 558/374; 558/303; 558/430
[58] Field of Search ......................................... 558/374

[56] References Cited

U.S. PATENT DOCUMENTS

| | | | |
|---|---|---|---|
| 2,623,060 | 12/1952 | Cragoe, Jr. ....................... | 558/374 |
| 2,655,526 | 10/1953 | Cope .................................. | 558/374 |
| 4,218,392 | 8/1988 | Lorenz et al. ...................... | 558/374 |
| 4,755,615 | 7/1988 | Kaufhold et al. .................. | 558/374 |

FOREIGN PATENT DOCUMENTS

| | | | |
|---|---|---|---|
| 512525 | 5/1955 | Canada ............................... | 558/374 |
| 532088 | 10/1956 | Canada ............................... | 558/374 |
| 693909 | 9/1964 | Canada ............................... | 558/374 |
| 49-92037 | 3/1974 | Japan .................................. | 558/374 |
| 606962 | 8/1948 | United Kingdom ............... | 558/374 |

*Primary Examiner*—Joseph Paul Brust
*Attorney, Agent, or Firm*—Oblon, Spivak, McClelland, Maier & Neustadt

[57] ABSTRACT

An improvement in a process for the industrial application of the Knoevenagel synthesis in an acid solution, resulting in a steady flow of waste gas.

7 Claims, No Drawings

PROCESS FOR INDUSTRIAL APPLICATION OF KNOEVENAGEL SYNTHESIS

BACKGROUND OF THE INVENTION

1. Field of the Invention

The invention relates to an improvement in a process for industrial application of Knoevenagel synthesis involving the condensation of cyanoacetic acid with ketones, e.g., cyclohexanone and cyclododecanone.

2. Discussion of the Background Knoevenagel synthesis has long been known to the art in the literature. A general summary can be found in Houben Weyl, Vol. 8, p. 450. Here the use of weak bases such as ammonia and primary and secondary amines is recommended as a particularly advantageous method of proceeding. In the same literature it is stated that the decarboxylation of the addition products first obtained is facilitated by basic catalysts.

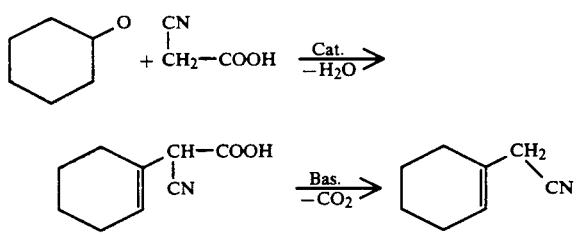

As an example, the reaction of cyclohexanone with cyanoacetic acid is described, using small quantities of ammonium acetate as a catalyst. The reaction takes place in two steps. The reaction product obtained from the first step must then be distilled carefully, because in the process carbon dioxide is violently evolved.

In Org. Synth. Coll., IV, pp. 234–236, this reaction with small quantities of catalyst and isolation of the intermediate, i.e., the cyclohexenyl cyanoacetic acid, is described precisely and in detail. Here, too, it is stated that decarboxylation occurs before or during distillation and then "very rapidly."

This vigorous generation of gas is not a problem in laboratory work, but stands in the way of industrial application, because such gas generation can lead to dangerous bursting of equipment due to sudden excess pressure. The pressure impact can, of course, be handled by high-pressure equipment, but this adds considerably to the cost.

All known processes for industrial use of Knoevenagel synthesis suffer from the disadvantage that they proceed too violently and unevenly and thus entail considerable technical expense for safety reasons. It would be desirable to develop a process whereby the waste gas could be controlled and whereby the waste gas was produced in an even flow without a great lapse of time, if possible immediately after combining the cyanoacetic acid and the ketone. In other words, the intermediate, in the case of cyclohexanone this would be cyclohexenyl cyanoacetic acid, should decarboxylate immediately.

According to Organikum, 12th Ed., VEB Deutscher Verlag der Wissenschaften, Berlin, 1973, p. 508, decarboxylation of the condensation product can be achieved in one step pursuant to a variation on Knoevenagel's process involving the use of amines such as pyridine in large quantities as a solvent with the additional admixture of piperidine. The use of these amines in large quantities makes the preparation of the reaction product much more costly, and problems of waste disposal arise. It would be a great technical advantage if rapid decarboxylation of the condensation product could be achieved without a basic solvent. Furthermore, there would be great interest in such a process by which Knoevenagel synthesis could be carried out on an industrial scale at low technical cost without a safety risk.

SUMMARY OF THE INVENTION

Accordingly, one object of the invention is to provide a way by which Knoevenagel synthesis can be performed in one step without incurring waste disposal problems and without incurring a safety risk due to decarboxylation.

The invention thus relates to an improvement in a process for industrial application of Knoevenagel synthesis involving the reaction of cyanoacetic acid with ketones in one step with the use of the conventional catalysts, wherein 1–10 moles of acetic acid are used per mole of ketone and added evenly in solution with the cyanoacetic acid to the ketone at 100–160° C., resulting in a controlled flow of waste gas.

DETAILED DESCRIPTION OF THE PREFERRED EMBODIMENTS

It has now been found that decarboxylation of the condensation products of, for example, cyclododecanone and cyanoacetic acid can take place even in an acid solution in the presence of acetic acid, and that by the use of relatively large quantities of acetic acid the generation of waste gas ($CO_2$) becomes steady and controllable and commences immediately upon combination of the input materials. This effect could not be anticipated, since, as mentioned above, the use of basic catalyst compounds is recommended to induce decarboxylation. In the above-mentioned operating instructions in the Organikum, it is stated that one can also add small quantities of acetic acid, but such small quantities serve only for the formation of salts and stabilization of the catalyst.

The process of the present invention cannot be achieved with the quantities of acetic acid recommended in the Organikum, namely, 0.2 moles per mole of ketone. The quantities of acetic acid must be much larger, namely, from 1 to 10 moles preferably from 1 to 5 moles, and more preferably 1 to 3 moles acetic acid per mole of ketone, the particularly preferred ratio being about 1.1:1. Additionally, with the process of the invention, one can dispense with the use of an entrainer (codistillation solvent) for separating the water produced.

A suitable amount of solid cyanoacetic acid can be dissolved in acetic acid, preferably in a weight ratio of approximately 1:1, yielding a preferred molar ratio of acetic acid to ketone of about 1.3:1. This solution, liquid at room temperature, is metered, with measurement of the waste gas, into the previously prepared ketone and catalyst. The preparation of this solution offers great advantages, since cyanoacetic acid decomposes at higher temperatures. When using the cyanoacetic acid as a melt, explosions can readily occur if the cyanoacetic acid is overheated at some point in the equipment because of some technical defect.

The reaction temperature is selected, within a range of about 100 to 160° C., depending on the reactivity of the particular ketone, so that when the solution of cyanoacetic acid in acetic acid is added waste gas forms. The preferred temperature range for cyclododecanone, for example, is about 130 to 140° C., and for cyclohexanone is about 100 to 120° C. Excessively high temperatures result in losses of yield due to decomposition of the cyanoacetic acid. Otherwise, the usual well known reaction parameters relating to catalyst, pressure, solvent, etc., used for Knoevenagel synthesis apply to the process of the invention.

As the ketone, aliphatic ketones, preferably $C_{3-20}$ aliphatic ketones, such as 3-octanone, 2-octanone, 2-heptanone, etc., cycloaliphatic ketones preferably $C_{3-20}$ cycloaliphatic ketones such as cyclohexanone, cycloheptanone, cyclododecanone, and alkyl-aryl-ketones, preferably $C_{7-30}$ alkyl-aryl-ketones such as acetophenone, benzophenone, and so forth, may be used. Having generally described this invention, a further understanding can be obtained by reference to certain specific examples which are provided herein for purposes of illustration only and are not intended to be limiting unless otherwise specified.

EXAMPLES

Reference Example 1

A glass apparatus having a four-necked flask was fitted with stirrer, thermometer, dropping funnel and distillation column with fitted water separator and reflux condenser with attached gas meter. The apparatus was loaded with:

| | |
|---|---|
| 910 g (5 moles) | cyclododecanone |
| 300 g | toluene |
| 20 g (0.259 moles) | ammonium acetate |

This mixture was heated with stirring to 132° C. 50 ml aliquots of a solution consisting in its entirety of:

| | |
|---|---|
| 389 g (4.3 moles) | cyanoacetic acid |
| 60.1 g (1.0 mole) | acetic acid | were added dropwise, and an acetic acid-water mixture was distilled off.

The quantity of waste gas given off every half hour was read on the gas meter (see column 6 in Table 1). Under column 5 is entered the quantity of waste gas that could potentially be created by reaction based on the quantity of input material. Column 7 shows the total quantities of waste gas given off. The smaller the difference between the values in columns 5 and 7, the smaller the danger of a sudden rise in pressure. It can be noted that the difference at the beginning, e.g., after the first and second hours, is quite great, whereas later, e.g., after the eighth and tenth hours, the difference is somewhat smaller. The amount of waste gas produced when the reaction mixture is cooled and then re-warmed, something that is sometimes necessary in industrial situations, is quite dramatic. See the figures after the second hour. The quantity of waste gas measured here would lead to a sudden increase in pressure, i.e., an explosion, in large industrial units.

After 16 hours the reaction was completed. The reaction output weighed 1,338 g. Gas chromatographic analysis showed that the reaction product was 27.8% cyclododecanone and 69.0% cyclododecenyl acetonitrile. This represents a 59.1% ketone conversion. The yield of nitrile with respect to converted ketone is 89.9%.

EXAMPLE 1

The apparatus described in Reference Example 1 was used and loaded with:

| | |
|---|---|
| 910 g (5.0 moles) | cyclododecanone |
| 20 g (0.259 moles) | ammonium acetate |

The mixture was heated with stirring to 140° C., while 50 ml aliquots of a solution consisting of:

| | |
|---|---|
| 389 g (4.3 moles) | cyanoacetic acid |
| 389 g (6.48 moles) | acetic acid | were added dropwise and an acetic acid-water mixture was distilled off.

Table 2 shows the progress of the reaction and gas generation. The values in column 5, in other words, the potential quantities of gas based on quantity of input materials, show surprisingly little difference from the figures in column 6, the sum of measured waste gas quantities. Even after shutting off and starting up again, as after the eighth hour, waste gas quantities produced are similar to those produced earlier. The waste gas quantities are very close to one another. In other words, an even flow of waste gas is quickly established, an important consideration for industrial operation.

After 16 hours the reaction was completed. The reaction output weighed 1,193 g. Gas chromatographic analysis showed that the reaction product was 29.6% cyclododecanone and 49.4% cyclododecenyl acetonitrile. This represents a 61.2% ketone conversion. The yield in nitrile based on converted ketone is 93.8%.

REFERENCE EXAMPLE 2

The apparatus described in Reference Example 1 was used and loaded with:

| | |
|---|---|
| 490 g (5.0 moles) | cyclohexanone |
| 20 g (0.259 moles) | ammonium acetate |

The mixture was heated with stirring to 120° C. and, 30 ml aliquots were added to a solution consisting of:

| | |
|---|---|
| 370 g (4.3 moles) | cyanoacetic acid |
| 60.1 g (1.0 mole) | acetic acid. |

Table 3 shows the progress of the reaction and gas generation as in the previous examples. It is obvious that after 3 hours there is large increase in gas generation, with twice the amount produced earlier. This problem makes industrial application impossible.

The yield of cyanohexenyl acetonitrile, calculated from the content determined by gas chromatography, was about 86%.

EXAMPLE 2

The apparatus described in Reference Example 1 was used and loaded with:

| | |
|---|---|
| 490 g (5.0 moles) | cyclohexanone |
| 20 g (0.259 moles) | ammonium acetate |

| -continued | |
|---|---|
| 50 g | cyclohexane. |

The mixture was heated with stirring to 100° C. and, 50 ml aliquots were added of a solution consisting of:

| 389 g (4.5 moles) | cyanoacetic acid |
|---|---|
| 389 g (6.48 moles) | acetic acid. |

The rest of the process proceeded as in Example 1. The results are shown in Table 4. In order to obtain a distillate at the low bottom temperature of 100° C., cyclohexane was added as indicated in the table. As Table 4 shows, a steady, controllable flow of waste gas was produced. The yield of cyclohexenyl acetonitrile was 91%.

EXAMPLE 3

The apparatus described in Reference Example 1 was used and loaded with the starting materials listed in Example 2 (ketone, cyclohexanone), with the difference that instead of 6.48 moles of acetic acid, 25.0 moles of acetic acid was used. The process was carried out as in Example 1.

The result was a steady, controllable flow of waste gas. The yield of cyclohexenyl acetonitrile was 83%.

EXAMPLE 4

The apparatus described in Reference Example 1 was used and loaded with:

| 600 g (5.0 moles) | acetophenone |
|---|---|
| 20 g (0.259 moles) | ammonium acetate |
| 50 g | cyclohexane. |

The mixture was heated with stirring to 120° C. and, as shown in Example 1, a mixture of

| 389 g (4.5 moles) | cyanoacetic acid |
|---|---|
| 389 g (6.48 moles) | acetic acid | was added dropwise. There resulted an even, controllable flow of gas. When the flow of gas dropped off, the temperature was raised to 130° C. and subsequently to 140° C. After 17 hours the reaction was completed. Processing by distillation supplied a 75% yield of 3-methyl cinnamic acid nitrile.

EXAMPLE 5

The apparatus described in Reference Example 1 was used and loaded with:

| 640 g (5.0 moles) | 3-octanone |
|---|---|
| 20 g (0.259 moles) | ammonium actetate |
| 50 g | cyclohexane |

The mixture was heated with stirring to 130° C. and, as shown in Example 1, a mixture of

| 389 g (4.5 moles) | cyanoacetic acid |
|---|---|
| 389 g (6.48 moles) | acetic acid | was added dropwise. There resulted a steady, controllable flow of gas. When the flow of gas dropped off, the temperature was raised to 140° C. After 20 hours the reaction was completed. Processing by distillation produced a 71% yield of beta-ethyl/beta-amyl-acrylonitrile as a mixture of isomers.

EXAMPLE 6

The apparatus described in Reference Example 1 was used and loaded with the products listed in Example 2 (ketone, cyclohexanone), except that instead of 0.259 moles of ammonium acetate, 0.3 moles of piperidine were used. The process was carried out as described in Example 1.

There resulted a steady, controllable flow of waste gas. The yield of cyclohexenyl acetonitrile was 86%.

Obviously, numerous modifications and variations of the present invention are possible in light of the above teachings. It is therefore to be understood that within the scope of the appended claims, the invention may be practiced otherwise than as specifically described herein.

TABLE 1

| 1 | 2 | Reference Example 1 | | | | |
|---|---|---|---|---|---|---|
| | | 3 | 4 | 5 | 6 | 7 |
| Time | Bottom | Input | | | Waste Gas | |
| (h) | Temp. (°C.) | ml ½ h | Total | Potential | L ½ h | Actual |
| Beg | 120 | — | — | — | — | — |
| ½ | 132 | 50 | 50 | 15.1 | 0.8 | 0.8 |
| 1 | " | 50 | 100 | 30.2 | 2.4 | 3.2 |
| ½ | 134 | 50 | 150 | 45.3 | 4.6 | 7.8 |
| 2 | " | — | 150 | 45.3 | 7.7 | 15.5 |
| Beg. | 134 | — | 150 | 45.3 | 3.0 | 18.5 |
| ½ | " | — | 150 | 45.3 | 19.5 | 38.0 |
| 3 | 136 | 30 | 180 | 54.5 | 3.0 | 41.0 |
| ½ | " | — | 180 | 54.5 | 3.6 | 44.6 |
| 4 | " | — | 180 | 54.5 | 0.5 | 45.1 |
| ½ | " | 30 | 210 | 63.6 | 4.3 | 49.3 |
| 5 | " | — | 210 | 63.6 | 2.8 | 52.1 |
| ½ | " | 30 | 240 | 72.6 | 0.1 | 52.2 |
| 6 | " | — | 240 | 72.6 | 3.5 | 55.7 |
| ½ | " | — | 240 | 72.6 | 4.2 | 59.9 |
| 7 | " | — | 240 | 72.6 | 0.2 | 60.1 |
| ½ | " | 30 | 270 | 81.7 | 4.0 | 64.1 |
| 8 | 137 | — | 270 | 81.7 | 2.0 | 66.1 |
| ½ | " | 30 | 300 | 90.8 | 2.8 | 68.9 |
| 9 | " | — | 300 | 90.8 | 3.6 | 72.5 |
| Beg. | 138 | — | 300 | 90.8 | 1.7 | 74.2 |
| ½ | 140 | — | 300 | 90.8 | 0.4 | 74.6 |
| 10 | " | 30 | 330 | 99.9 | 1.5 | 76.1 |
| ½ | " | — | 330 | 99.9 | 2.0 | 78.1 |
| 11 | " | 30 | 360 | 109.0 | 1.1 | 79.2 |
| ½ | " | 10 | 370 | 112.0 | 0.9 | 80.1 |
| 12 | " | | | 112.0 | 0.9 | 81.0 |
| ½ | " | | | 112.0 | 0.6 | 81.6 |
| 13 | " | | | 112.0 | 0.8 | 82.4 |
| ½ | " | | | 112.0 | 0.7 | 83.1 |
| 14 | " | | | 112.0 | 0.7 | 83.8 |
| ½ | " | | | 112.0 | 0.6 | 84.4 |
| 15 | " | | | 112.0 | 0.5 | 84.9 |
| ½ | " | | | 112.0 | 0.3 | 85.1 |
| 16 | " | | | 112.0 | 0.2 | 85.3 |

TABLE 2

| 1 | 2 | Example 1 | | | | |
|---|---|---|---|---|---|---|
| | | 3 | 4 | 5 | 6 | 7 |
| Time | Bottom | Input | | | Waste Gas | |
| (h) | Temp. (°C.) | ml ½ h | Total | Potential | Actual | L ½ h |
| Beg. | 140 | — | — | — | — | — |
| ½ | " | 50 | 50 | 7.4 | 6.3 | 6.3 |
| 1 | " | 50 | 100 | 14.7 | 14.0 | 7.7 |
| ½ | " | 50 | 150 | 22.1 | 21.6 | 7.6 |
| 2 | " | 50 | 200 | 29.5 | 29.6 | 8.0 |
| ½ | " | 50 | 250 | 36.8 | 36.8 | 7.2 |
| 3 | " | 50 | 300 | 44.2 | 43.9 | 7.1 |
| ½ | " | 50 | 350 | 51.6 | 51.3 | 7.4 |
| 4 | " | 50 | 400 | 59.0 | 56.1 | 4.8 |

TABLE 2-continued

Example 1

| 1 Time (h) | 2 Bottom Temp. (°C.) | 3 Input ml ½ h | 4 Input Total | 5 Waste Gas Potential | 6 Waste Gas Actual | 7 L ½ h |
|---|---|---|---|---|---|---|
| ½ | " | 50 | 450 | 66.3 | 58.8 | 2.7 |
| 5 | " | — | 450 | 66.3 | 62.0 | 3.2 |
| ½ | " | — | 450 | 66.3 | 64.0 | 2.0 |
| 6 | " | 50 | 500 | 73.7 | 65.2 | 1.2 |
| ½ | " | — | 500 | 73.7 | 66.2 | 1.0 |
| 7 | " | — | 500 | 73.7 | 67.3 | 1.1 |
| ½ | " | 50 | 550 | 81.1 | 67.9 | 0.6 |
| 8 | " | — | 550 | 81.1 | 68.9 | 1.0 |
| Beg. | 132 | — | 550 | 81.1 | 68.9 | — |
| ½ | 140 | — | 550 | 81.1 | 69.2 | 0.3 |
| 9 | " | — | 550 | 81.1 | 70.2 | 1.0 |
| ½ | " | — | 550 | 81.1 | 71.3 | 1.1 |
| 10 | " | — | 550 | 81.1 | 72.3 | 1.0 |
| ½ | " | — | 550 | 81.1 | 73.3 | 1.0 |
| 11 | " | — | 550 | 81.1 | 74.2 | 0.9 |
| ½ | " | — | 550 | 81.1 | 74.6 | 0.4 |
| 12 | " | 50 | 600 | 88.4 | 75.5 | 0.9 |
| ½ | " | — | 600 | 88.4 | 76.0 | 0.5 |
| 13 | " | 50 | 650 | 95.8 | 77.0 | 1.0 |
| ½ | " | 20 | 670 | 98.7 | 78.2 | 1.2 |
| 14 | " | | | 98.7 | 79.4 | 1.2 |
| ½ | " | | | 98.7 | 80.6 | 1.2 |
| 15 | " | | | 98.7 | 81.7 | 1.1 |
| ½ | " | | | 98.7 | 83.0 | 1.3 |
| 16 | " | | | 98.7 | 84.0 | 1.4 |

TABLE 3

Reference Example 2

| 1 Time | 2 Bottom Temp. (°C.) | 3 Input ml/h | 4 Input Total | 5 Waste Gas Potential | 6 Waste Gas Actual | 7 L ½ h |
|---|---|---|---|---|---|---|
| Beg. | 120 | — | — | — | — | — |
| ½ | " | 30 | 30 | 8.6 | 7.1 | 7.1 |
| 1 | " | 30 | 60 | 17.2 | 14.5 | 7.4 |
| ½ | " | 30 | 90 | 25.6 | 22.7 | 8.2 |
| 2 | " | 30 | 120 | 34.3 | 31.0 | 8.3 |
| ½ | " | 30 | 150 | 42.9 | 39.0 | 8.0 |
| 3 | " | 30 | 180 | 51.5 | 57.4 | 18.4 |
| ½ | " | — | 180 | 51.5 | 58.0 | 0.6 |
| Beg. | " | — | 180 | 51.5 | 58.0 | — |
| 4 | " | 30 | 210 | 60.1 | 64.5 | 6.5 |
| ½ | " | 30 | 240 | 68.7 | 71.0 | 6.5 |
| 5 | " | 30 | 270 | 77.3 | 78.3 | 6.3 |
| ½ | " | 30 | 300 | 85.3 | 84.5 | 6.2 |
| 6 | 118 | — | 300 | 85.3 | 86.1 | 1.6 |
| ½ | 116 | 30 | 330 | 94.4 | 91.2 | 5.1 |
| 7 | 114 | — | 330 | 94.4 | 92.4 | 1.2 |
| ½ | " | 30 | 360 | 103.0 | 96.2 | 3.8 |
| 8 | " | | | 103.0 | 98.5 | 2.3 |
| ½ | 112 | | | 103.0 | 99.1 | 0.6 |
| 9 | " | | | 103.0 | 99.2 | 0.1 |
| ½ | " | | | 103.0 | 99.2 | 0.0 |

TABLE 4

Example 3

| 1 Time | 2 Bottom Temp. (°C.) | 3 Input ml ½ h | 4 Input Total | 5 Waste Gas Pot. | 6 Waste Gas Act. | 7 Cyclohexane Added |
|---|---|---|---|---|---|---|
| Beg. | 100 | — | — | — | — | |

TABLE 4-continued

Example 3

| 1 Time | 2 Bottom Temp. (°C.) | 3 Input ml ½ h | 4 Input Total | 5 Waste Gas Pot. | 6 Waste Gas Act. | 7 Cyclohexane Added |
|---|---|---|---|---|---|---|
| ½ | " | 50 | 50 | 8.0 | 5.9 | 5.9 |
| 1 | " | 50 | 100 | 16.0 | 13.2 | 6.3 | 25 g |
| ½ | " | 50 | 150 | 24.0 | 20.7 | 7.5 | |
| 2 | " | 50 | 200 | 32.0 | 27.9 | 7.2 | |
| ½ | " | 50 | 250 | 40.0 | 33.7 | 5.8 | |
| 3 | " | 50 | 300 | 48.0 | 38.4 | 4.7 | |
| ½ | " | — | 300 | 48.0 | 41.7 | 3.3 | 25 g |
| 4 | " | — | 300 | 48.0 | 42.3 | 0.6 | |
| ½ | " | 50 | 350 | 56.0 | 45.8 | 3.5 | |
| 5 | " | — | 350 | 56.0 | 47.7 | 1.9 | |
| ½ | " | — | 350 | 56.0 | 48.5 | 0.8 | 25 g |
| 6 | " | 50 | 400 | 64.0 | 50.9 | 2.4 | |
| Beg. | " | — | 400 | 64.0 | — | — | |
| ½ | " | — | 400 | 64.0 | 54.9 | 4.4 | |
| 7 | " | 50 | 450 | 72.0 | 57.8 | 2.9 | |
| ½ | " | 50 | 500 | 80.0 | 59.5 | 1.7 | |
| 8 | " | — | 500 | 80.0 | 62.9 | 3.4 | |
| ½ | " | — | 500 | 80.0 | 66.2 | 3.3 | |
| 9 | " | 50 | 550 | 88.0 | 67.9 | 1.7 | |
| ½ | " | — | 550 | 88.0 | 69.9 | 2.0 | |
| 10 | " | — | 550 | 88.0 | 71.8 | 1.9 | |
| ½ | " | — | 550 | 88.0 | 73.1 | 1.3 | |
| 11 | " | 50 | 600 | 96.0 | 73.9 | 0.8 | 25 g |
| ½ | " | — | 600 | 96.0 | 74.9 | 1.0 | |
| 12 | " | — | 600 | 96.0 | 76.6 | 1.7 | |
| ½ | " | — | 600 | 96.0 | 77.1 | 1.1 | |
| 13 | " | 50 | 650 | 104.0 | 78.3 | 0.6 | |
| ½ | " | — | 650 | 104.0 | 79.1 | 0.8 | |
| 14 | " | 30 | 680 | 108.5 | 79.9 | 0.8 | |
| Beg. | " | | | 108.5 | 80.8 | 0.9 | |
| ½ | " | | | 108.5 | 81.2 | 0.4 | |
| 15 | " | | | 108.5 | 82.0 | 0.8 | |
| ½ | " | | | 108.5 | 82.8 | 0.8 | |
| 16 | " | | | 108.5 | 83.7 | 0.9 | |
| ½ | " | | | 108.5 | 84.1 | 0.4 | |
| 17 | " | | | 108.5 | 84.5 | 0.4 | |
| ½ | " | | | 108.5 | 84.9 | 0.4 | |

What is new and desired to be secured by Letters Patent of the United States is:

1. In a Knoevenagel synthesis involving reaction of cyanoacetic acid with a ketone followed by decarboxylation in one step with a Knoevenagel synthesis catalyst, the improvement comprising adding in portions 1–10 moles of acetic acid in solution with said cyanoacetic acid per mole of ketone, to the ketone and catalyst at about 100–160° C., wherein the addition of said portions produced a controlled even flow of $CO_2$ waste gas.

2. The process of claim 1, wherein 1–5 moles of acetic acid are used per mole of ketone.

3. The process of claim 1, wherein 1–3 moles of acetic acid are used per mole of ketone.

4. The process of claim 1, wherein said ketone of an aliphatic ketone, cycloaliphatic ketone or alkyl-aryl-ketone.

5. The process of claim 4, wherein said ketone is selected from the group consisting of $C_{3-20}$ aliphatic ketones, $C_{3-20}$ cycloaliphatic ketones and $C_{7-30}$ alkyl-aryl-ketones.

6. The process of claim 1, wherein said ketone is cyclododecanone and the process is conducted at about 130–140° C.

7. The process of claim 1, wherein said ketone is cyclohexanone and said process is conducted at about 100–120° C.

* * * * *